United States Patent [19]

Suzuki et al.

[11] Patent Number: 4,799,950
[45] Date of Patent: Jan. 24, 1989

[54] PLANT GROWTH REGULATING COMPOSITION

[75] Inventors: Akinori Suzuki, Chiba; Suong Be Hyeon, Urawa; Toshio Kajita, Yachiyo; Masakazu Furushima, Nagareyama; Akinori Tanaka, Niigata, all of Japan

[73] Assignee: Mitsubishi Gas Chemical Company, Inc., Tokyo, Japan

[21] Appl. No.: 5,279

[22] Filed: Jan. 20, 1987

[30] Foreign Application Priority Data

Jan. 21, 1986 [JP] Japan ................................. 61-8978

[51] Int. Cl.$^4$ ............................................. A01N 43/08
[52] U.S. Cl. ............................................. 71/89; 71/76; 71/121
[58] Field of Search ............................ 71/121, 89, 76

[56] References Cited

U.S. PATENT DOCUMENTS

| | | | |
|---|---|---|---|
| 3,038,794 | 6/1962 | Geary et al. | 71/89 |
| 3,102,017 | 8/1963 | Shurter et al. | 71/89 |
| 3,118,753 | 1/1964 | Shive et al. | 71/89 |
| 3,395,009 | 7/1968 | Oettel et al. | 71/121 |
| 3,482,961 | 12/1969 | Nickell et al. | 71/121 |
| 4,309,205 | 1/1982 | Kessler | 71/121 |

*Primary Examiner*—Glennon H. Hollrah
*Assistant Examiner*—A. A. Owens
*Attorney, Agent, or Firm*—Wenderoth, Lind & Ponack

[57] ABSTRACT

A plant growth regulating composition comprising as an active ingredient a combination of
(a) at least one gibberellin-type plant hormone, and
(b) at least one compound selected from compounds of the general formula

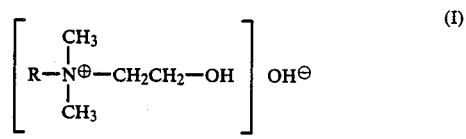

wherein R represents a $C_1$–$C_5$ alkyl, $C_2$–$C_5$ alkenyl, $C_2$–$C_5$ alkynyl, $C_1$–$C_5$ haloalkyl or benzyl group, and agriculturally acceptable salts thereof.

7 Claims, No Drawings

PLANT GROWTH REGULATING COMPOSITION

This invention relates to a plant growth regulating composition, and more specifically, to a composition comprising a combination of a gibberellin, a kind of a plant hormone, and a certain choline analogous compound and having remarkable synergistic plant growth regulating activities such as promotion of growth, germination, root formation and thickening growth.

Heretofore, gibberellins having growth promoting activity, auxins having root formation promoting activity such as indoleacetic acid and alpha-naphthaleneacetic acid, cytokinins having aging preventing activity such as kinetin (6-furfurylaminopurine) and benzyladenine, and ethylenes having defoliating activity such as ethylene and ethephon (tradename Ethrel) have been known as plant hormone-type plant growth regulators in practical use.

In particular, gibberellins are much used for seedless grapes (Delaware variety). Attempts have recently been made to use gibberellins in other applications, for example to control olecollosis on citrus fruits by taking advantage of their excellent growth promoting activity, activity on flowering, dormancy breaking activity, activity on germination and parthenocarpy promoting activity. Since, however, gibberellins are expensive, considerable restrictions are imposed on their use.

On the other hand, choline salts are known to have a plant growth promoting effect. U.S. Pat. No. 4,309,205 discloses a method of increasing the quantity and quality of flowers and fruits of a plant growing in soil which comprises applying to a mature plant during its reproductive stage a flower or fruit quantity and quality improving effective amount of at least one non-toxic salt of choline in an aqueous medium.

The present inventors further made investigations on the plant growth promoting effects of these choline salts, and found that certain choline analogous compounds have plant growth promoting activities, for example they promote photosynthesis of wheat and root formation of rice and have an effect of increasing the harvest of crops such as onion, sweet potato and potato (see U.S. patent applications Ser. Nos. 674,973 and 870,394 filed respectively on Nov. 26, 1984 and June 4, 1986; and European Patent Applications Nos. 84114265.6 and 86107622.2).

The present inventors continued their research on the plant growth promoting effects of the choline analogs, and have now found unexpectedly that when a certain choline analog is combined with a gibberellin-type plant hormone, the plant growth regulating actions of the respective compounds are increased synergistically, and the combination of them exhibits a marked synergistic effect not seen in the case of using them individually.

According to this invention, there is provided a plant growth regulating composition comprising as an active ingredient a combination of (a) at least one gibberellin-type plant hormone, and
(b) at least one compound (to be referred to as "choline analog") selected from compounds of the general formula

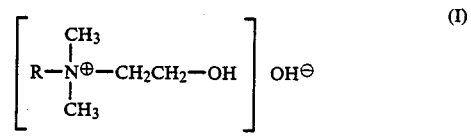

wherein R represents a $C_1$-$C_5$ alkyl, $C_2$-$C_5$ alkenyl, $C_2$-$C_5$ alkynyl, $C_1$-$C_5$ haloalkyl or benzyl group, and agriculturally acceptable salts thereof.

The "gibberellin-type plant hormone" used as one active component of the plant growth regulating composition of this invention is described at page 631 of Merck Index, 10th edition, and more than 60 giberrellins are known. $GA_3$, $GA_4$ and $GA_7$ are especially preferred because of their high activity on plants and ready availability.

The choline analog used in combination with the gibberellin-type plant hormone in this invention is a compound of general formula (I) or its agriculturally acceptable salt.

In formula (I), the $C_{1-5}$ alkyl group represented by R may be linear or branched, and includes, for example, methyl, ethyl, n-propyl, iso-propyl, n-butyl, isobutyl, sec-butyl, tert-butyl, n-pentyl and tert-pentyl. The $C_{2-5}$ alkenyl may also be linear or branched, and includes, for example, vinyl, allyl, methallyl, 2-butenyl, 3-butenyl, and 2-(3-methyl)butenyl. Examples of the $C_{2-5}$ alkynyl group are ethynyl, 2-propynyl and butynyl. Examples of the $C_1$-$C_5$ haloalkyl are 2-chloroethyl and 3-chloropropyl.

Methyl, ethyl, butyl and benzyl groups are especially preferred as R.

The agriculturally acceptable salts of the compounds of formula (I) include, for example, hydrohalogenates such as hydrochlorides and hydrobromides, inorganic acid salts such as phosphates, nitrates, sulfates and carbonates, and organic acid salts such as acetates, citrates, lactates and L(+)-tartrates. Of these, the hydrochlorides and hydrobromides are preferred.

The compounds of formula (I) or its salt can be produced, for example, by reacting an N,N-dimethylethanolamine represented by the formula

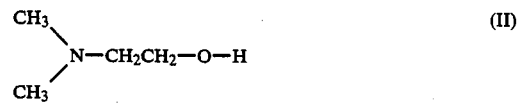

with a halide represented by the formula

wherein Hal represents a halogen atom, and R is as defined above,
to obtain a compound represented by the following formula

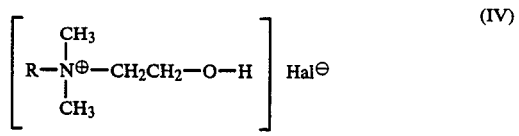

wherein R is as defined above, and if desired, converting Hal⊖ in the resulting compound of formula (IV) into a hydroxyl ion or another suitable salt anion.

Some embodiments of their production are shown below.

PRODUCTION EXAMPLE 1

A 100 ml eggplant-shaped flask was charged with 8.91 g of N,N-dimethylethanolamine, and 30 ml of diethyl ether was added. The mixture was stirred, and 11.45 g of allyl chloride was added. The mixture was stirred at room temperature for 2 days. The resulting white precipitate was collected by suction filtration, well washed with dimethyl ether, and dried in a desiccator under reduced pressure to give 9.01 g (yield 55%) of a compound of the following formula

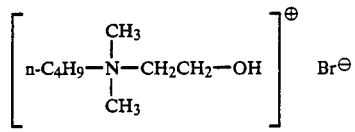

(compound No. 3 in Table 1 given hereinbelow).

In the same way as in Production Examples 1 and 2, the compounds of formula (I) or salts thereof shown in Table 1 can be obtained. Table 1 also describes the compounds obtained in Production Examples 1 and 2.

TABLE 1

$$\left[ R-\overset{\overset{CH_3}{|}}{\underset{\underset{CH_3}{|}}{N^{\oplus}}}-CH_2CH_2-OH \right] X^{\ominus}$$

| Compound No. | R | Salt X | OH stretching | CH deformation | C—O stretching | Others |
|---|---|---|---|---|---|---|
| 1 | $C_2H_5-$ | Br | 3650–3050 | 1460 | 1080 | |
| 2 | $\begin{array}{c}CH_3\\ \phantom{C}\diagdown\\ \phantom{CH_3}CH-\\ \phantom{C}\diagup\\ CH_3\end{array}$ | Br | 3650–3050 | 1475 | 1080 | |
| 3 | $CH_3CH_2CH_2CH_2-$ | Br | 3650–3050 | 1485 | 1045 | |
| 4 | $CH_2=CHCH_2-$ | Cl | 3650–3000 | 1460 / 950 | 1080 | C=C stretching 1640 |
| 5 | $CH_3CH_2CH_2-$ | Br | 3650–3050 | 1460 | 1070 | |
| 6 | $CH_2=C(CH_3)CH-$ | Br | 3650–3050 | 1470 / 930 | 1080 | C=C stretching 1635 |
| 7 | $Cl-CH_2CH_2CH_2-$ | Br | 3220 | 1464 | 1088 | |
| 8 | ⌬—$CH_2-$ | Cl | 3300 | 1475 | 1088 | |
| 9 | $Cl-CH_2CH_2-$ | Br | 3250 | 1456 | 1090 | |
| 10 | $(CH_3)_3C-$ | Br | 3650–3100 | 1470 | 1080 | |
| 11 | $CH\equiv CCH_2-$ | Br | 3650–3050 | 1455 | 1085 | C=C stretching 2130 |
| 12 | $CH_3CH=CHCH_2-$ | Br | 3650–3080 | 1460 | 1090 | |
| 13 | $CH_3CH_2CH_2-C(CH_3)_2-$ | Br | 3650–3010 | 1470 | 1080 | |
| 14 | $CH_3-$ | Cl | 3240 | 1468 | 1084 | |

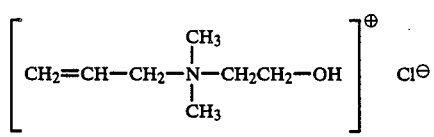

(compound No. 4 in Table 1 given hereinbelow).

PRODUCTION EXAMPLE 2

A 50 ml eggplant-shaped flask was charged with 4.46 g of N,N-dimethylethanolamine and 7.0 g of n-butyl bromide, and the mixture was stirred at room temperature for 15 hours, and then worked up as in Production Example 1 to give 10.46 g (yield 93%) of a compound of the following formula

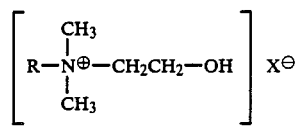

Compounds Nos. 1, 3, 8 and 14 are particularly preferred among these choline analogs. These compounds may be used singly or in combination.

In the composition of this invention, the mixing ratio between the gibberellin-type plant hormone and the choline analog cannot be generally fixed, and may be varied depending upon a plant to which the composition is to be applied. The optimum mixing ratio would be able to be determined easily by those skilled in the art by a pot test or in a small-scale field test. Generally, the convenient weight ratio of the gibberellin-type plant hormone to the choline analog is considered to be from 1:0.02 to 1:2,000, preferably from 1:0.05 to 1:1,000, more preferably from 1:0.1 to 1:100.

The gibberellin-type plant hormone used as an active ingredient in the composition of this invention has plant growth promoting activity, activity on flowering, dormancy breaking activity, activity on germination, parthenocarpy promoting activity and alpha-amylase activating action. On the other hand, much is still unknown of the activity of the choline analogs on plants, but the present inventors have confirmed that these choline analogs have growth promoting activity, root formation promoting activity, photosynthesis promoting activity, alpha-amylase activating action, fruit coloration promoting activity, fruit thickening promoting activity.

When the gibberellin-type plant hormone and the choline analog having these activities are applied in combination to plants, the activities of the respective components are synergistically increased and the amount of the expensive gibberellin-type plant hormone to be used can be markedly decreased. In addition, marked plant growth promoting, germination promoting and thickening growth promoting effects, which cannot at all be achieved by the use of these components singly, can be obtained.

There is no strict limitation on plants on which the composition of this invention exhibits the above effects upon application, and the composition of this invention is effective on a wide variety of agriculturally or horticulturally cultivated plants. Specific examples include cereal plants such as rice, wheat, barley, and corn, leguminous plants such as soybean; plants having underground tubers or bulbs such as onion, garlic and potato; vegetables grown for their edible roots such as beet and carrot; fruits such as peach, persimmon, grape and apple; vegetables grown for their edible fruits such as tomato and cucumber; vegetable grown for their edible leaves such as lettuce, cabbage, cauliflower, mustard and spinach; and flowers such as tulip and cosmos.

The composition of this invention may be formulated for application in any known form, such as a wettable powder, granules, an aqueous solution, an emulsifiable concentrate or an aqueous suspension, using conventional agriculturally acceptable carriers or diluents. There is no special restriction on the carriers or diluents used in the formulation so long as they are agriculturally acceptable. For example, talc and bentonite may be used as a carrier for a wettable powders and granules. The aqueous solution or suspension is most preferred and convenient as the form in which the composition is applied.

The resulting formulation may generally contain 0.1 to 70% by weight, preferably 0.5 to 50% by weight, based on its weight, of the gibberellin-type plant hormone and the choline analog, depending upon the form of the formulation. Such formulations may further contain another conventional agriculturally active ingredient such as a fertilizer, insecticide, fungicide or bactericide.

The formulations may desirably contain a surfactant. The amount of the surfactant is, for example, 0.02 to 20% by weight, preferably 0.1 to 5% by weight, depending upon the form of the formulation to promote the adsorption and penetration of the active ingredients. Preferred surfactants may include nonionic surfactants such as polyoxyethylene alkyl ethers (e.g., polyoxyethylene lauryl ether), and anionic surfactants such as lauryl sulfonate triethanolamine salt.

The composition of this invention may be applied by any methods known per se. For example, it may be sprayed onto the stalks and leaves of mature plants, or poured onto parts near the roots. Seeds are preferably immersed in a solution containing the gibberellin-type plant hormone and the choline analog in accordance with this invention.

The rate of application of the combination of the gibberellin-type plant hormone and the choline analog in accordance with this invention varies, for example, with the type of a plant to be treated, the stage of plant growth, and the manner and timing of application. For example, when the composition of this invention is to be applied in the form of an aqueous solution or suspension, it is convenient that the gibberellin-type plant hormone is present in a concentration of generally 1 to 1000 ppm, preferably 2 to 500 ppm, and the choline analog, in a concentration of generally 1 to 3,000 ppm, preferably 10 to 2,000 ppm, in the solution or suspension.

The manner and timing of applying the composition of this invention to plants differ depending upon the kind of a plant to be treated, and are difficult to determine definitely. Generally, however, it is desirably applied at some point during a period from the reproductive growth to the harvesting time. To some plants, however, application during vegetative growth may provide more desirable effects. In other words, there is no specific limit to the timing of application.

For example, to maintain the freshness of persimmon, it is suitable to spray the composition to the fruits and the surfaces of the leaves from about 20 days before the scheduled date of harvesting to the day before the day of harvesting. The concentration of the gibberellin is 10 to 100 ppm, and the concentration of the choline is 10 to 2000 ppm. The rate of spraying is 50 to 500 liters/10a, and the spraying is carried out once or twice a day.

For the purpose of berry thickening and berry dropping prevention of grapes, it is advisable to spray the formulation onto the corollas after berry formation or to immerse the corollas in the formulation. The concentration of the gibberellin is 10 to 100 ppm, and the concentration of the choline is 10 to 2000 ppm. The rate of spraying is 50 to 200 liters/10a. In the case of immersion, the amount of the formulation can be very small.

For the purpose of promoting germination and growth of corn and wheat, a great effect can be obtained by immersing the seeds in the formulation for 3 to 24 hours before sowing. In this case, the concentration of the gibberellin is 20 to 300 ppm, and the concentration of the choline is 100 to 1000 ppm.

For promoting germination and growth of mustard, tomato and lettuce, it is advisable to immerse the seeds in the formulation for about 3 to 24 hours before sowing. In this case, the concentration of the gibberellin is 10 to 300 ppm, and the concentration of the choline is 1 to 100 ppm. Preferably, the treated seeds are washed with water after immersion.

For application of the composition of the invention to plants, it may be formulated into a wettable powder, an aqueous solution, a suspension in water or oil, etc. Typical formulation examples are given below.

FORMULATION EXAMPLE 1

Wettable powder:-

| | |
|---|---|
| Gibberellin ($A_3$) | 3 parts by weight |
| Compound No. 14 (choline chloride) | 10 parts by weight |
| Sodium dodecylbenzenesulfonate | 2 parts by weight |
| Polyoxyethylene alkyl aryl ether | 1 parts by weight |
| Talc | 60 parts by weight |

-continued

| FORMULATION EXAMPLE 1 | |
|---|---|
| Bentonite | 24 parts by weight |

The above ingredients are uniformly mixed and pulverized to form a wettable powder. Generally, the wettable powder is used after diluting it with water to 150 to 2,000 times.

| FORMULATION EXAMPLE 2 | |
|---|---|
| Aqueous solution:- | |
| Gibberellin (A$_3$) | 1 part by weight |
| Compound No. 14 (75% aqueous solution of choline chloride) | 3 part by weight |
| Polyoxyethylene alkyl aryl ether | 1 part by weight |
| Lauryl methyl dihydroxyethyl ammonium chloride | 1 part by weight |
| Water | 94 part by weight |

The above ingredients were uniformly mixed to form an aqueous solution.

The excellent plant growth regulating activity of the composition of this invention will be demonstrated by the following Test Examples.

TEST EXAMPLE 1

Seeds of dwarf rice (variety: "tangin bozu") were sown at a rate of 20 on absorbent cotton pieces containing an aqueous solution of each of the test chemicals in the concentrations indicated in Table 2 in a high-skirted petri dish.

The petri dish was placed in a phytotron at 25° C. and 5000 luxes, and cultivated for 10 days. The heights of the grown rice plants were measured, and the results are shown in Table 2.

It is seen from the results that compound No. 14 (choline chloride) alone hardly affected the plant's height, but when it is used in combination with gibberellin A$_3$, a marked height increasing effect can be obtained.

TABLE 2

| Test chemical | Ratio of the plant height based on the non-treated area (%) |
|---|---|
| Non-treated (treated with water) | 100 (3.7 cm) |
| Compound No. 14, 1 ppm | 101 |
| Compound No. 14, 10 ppm | 102 |
| Compound No. 14, 100 ppm | 98 |
| Gibberellin, 1 ppm | 165 |
| Gibberellin 1 ppm + Compound No. 14 1 ppm | 197 |
| Gibberellin 1 ppm + Compound No. 14 10 ppm | 197 |
| Gibberellin 1 ppm + Compound No. 14 100 ppm | 218 |
| Gibberellin, 10 ppm | 206 |
| Gibberellin 10 ppm + Compound No. 14 1 ppm | 214 |
| Gibberellin 10 ppm + Compound No. 14 10 ppm | 214 |
| Gibberellin 10 ppm + Compound No. 14 100 ppm | 247 |

TEST EXAMPLE 2

Seeds of lettuce (variety: "Imperial 44") and leaf mustard were immersed at 10 to 25° C. for 24 hours in each of the aqueous solutions of gibberellin A$_3$, compound No. 1, compound No. 4 and compound No. 14 either alone or in combination in the concentrations indicated in Table 3, and then dried in the air until the seed surfaces became dry.

The seeds were then sown uniformly in plastic pots filled with soil at a rate of 100 per pot.

The plants were then cultivated for 10 days in a greenhouse, and the rate of germination was measured. The results are shown in Table 3.

TABLE 3

| | Rate of germination (%) | |
|---|---|---|
| Test chemical | lettuce | mustard |
| Non-treated (treated with water) | 9 | 5 |
| Compound No. 1, 300 ppm | 62 | 54 |
| Compound No. 4, 300 ppm | 65 | 61 |
| Compound No. 14, 300 ppm | 75 | 76 |
| Gibberellin, 50 ppm | 59 | 70 |
| Gibberellin, 100 ppm | 68 | 76 |
| Gibberellin 50 ppm + Compound No. 1 300 ppm | 99 | 99 |
| Gibberellin 100 ppm + Compound No. 1 300 ppm | 98 | 99 |
| Gibberellin 50 ppm + Compound No. 4 300 ppm | 98 | 98 |
| Gibberellin 100 ppm + Compound No. 4 300 ppm | 99 | 97 |
| Gibberellin 50 ppm + Compound No. 14 300 ppm | 100 | 99 |
| Gibberellin 100 ppm + Compound No. 14 300 ppm | 98 | 100 |

TEST EXAMPLE 3

Each of the test chemicals (containing 2% polyoxyethylene alkyl aryl ether as a spreader) in the concentrations shown in Table 4 was sprayed onto the corollas of grape (variety: "kyoho") 30 days (on July 18) after full bloom. The grape was harvested on September 5, and the sweetness degree and weight of the berries were measured. Furthermore, on September 20, the rate of berry dropping was determined. The results are shown in Table 4.

TABLE 4

| Test chemicals | Sweetness degree (g/100 ml) | Weight (% based on the non-treated area) | Rate of berry dropping (%) |
|---|---|---|---|
| Non-treated | 13.6 | 100 (4.6 g) | 25 |
| Compound No. 6, 300 ppm | 13.2 | 100 | 17 |
| Compound No. 14, 1000 ppm | 13.6 | 108 | 9 |
| Compound 14, (1500 ppm) | 13.6 | 100 | 4 |
| Gibberellin (A$_3$), (100 ppm) | 13.1 | 125 | 20 |
| Gibberellin (A$_3$), (200 ppm) | 13.0 | 125 | 19 |
| Gibberellin (A$_3$) (100 ppm) + compound No. 6 (300 ppm) | 13.2 | 125 | 0 |
| Gibberellin (A$_3$) (100 ppm) + compound No. 14 (1000 ppm) | 13.6 | 145 | 6 |
| Gibberellin (A$_3$) | 13.6 | 147 | 3 |

TABLE 4-continued

| Test chemicals | Sweetness degree (g/100 ml) | Weight (% based on the non-treated area) | Rate of berry dropping (%) |
| --- | --- | --- | --- |
| (100 ppm) + compound No. 14 (1500 ppm) | | | |
| Gibberellin (A$_3$) (200 ppm) + compound No. 14 (1000 ppm) | 13.6 | 139 | 3 |
| Gibberellin (A$_3$) (200 ppm) + compound No. 14 (1500 ppm) | 13.6 | 140 | 0 |

TEST EXAMPLE 4

Seeds of dwarf rice (variety "tangin bozu") were sown at a rate of 20 in an agar medium containing each of the test chemicals in the concentrations indicated in Table 5 put in a high-skirted petri dish.

The petri dish was placed in a phytotron at 25° C. and 5000 lux, and the rice was cultivated for 10 days. The length of the second leaf sheath of the grown rice was measured. The results are shown in Table 5.

It is seen from the results that compounds Nos. 1, 3, 4 and 8 hardly affected the length of the second leaf sheath when used singly, but when they are used in combination with gibberellins, a marked effect of growing the leaf sheath length can be obtained.

TABLE 5

| Test chemicals | Length of the second leaf sheath (ratio to the non-treated area) |
| --- | --- |
| Compound No. 1, 10 ppm | 103 |
| Compound No. 3, 10 ppm | 101 |
| Compound No. 4, 10 ppm | 100 |
| Compound No. 8, 10 ppm | 100 |
| Gibberellin, 1 ppm | 143 |
| Gibberellin 1 ppm + compound No. 1 10 ppm | 241 |
| Gibberellin 1 ppm + compound No. 3 10 ppm | 239 |
| Gibberellin 1 ppm + compound No. 4 10 ppm | 258 |
| Gibberellin 1 ppm + compound No. 8 10 ppm | 199 |
| Non-treated area | 100 |

We claim:

1. A plant growth regulating composition for the promotion of growth, germination, root formation and thickening growth, said composition comprising as an active ingredient a combination of
   (a) at least one gibberellin-type plant hormone selected from the group consisting of gibberellin A$_3$ and gibberellin A$_4$, and
   (b) at leat one compound selected from the compounds of the general formula

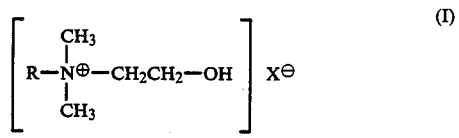

wherein R represents a C$_1$–C$_5$ alkyl, C$_2$–C$_5$ alkenyl, C$_2$–C$_5$ alkynyl or benzyl group, and X represents a hydroxy group or chlorine or bromine atom,
wherein the weight ratio of the gibberellin type plant hormone to the compound of the above formula (I) is from 1:0.1 to 1:100.

2. A composition of claim 1 wherein the gibberellin-type plant hormone is gibberellin A$_3$.

3. A composition of claim 1 wherein R represents a methyl, ethyl, butyl or benzyl group.

4. A composition of claim 1 which is in the form of a wettable powder or an aqueous solution or suspension.

5. A method of regulating the growth of a plant, which comprises applying an effective amount of the composition of claim 1 to the stalks, leaves, roots, fruits or seeds of the plant.

6. A method of claim 5 in which the composition of claim 1 is in the form of an aqueous solution or suspension.

7. A method of claim 6 wherein the concentration of the gibberellin-type plant hormone in the aqueous solution or suspension is 1 to 1000 ppm, and the concentration of the compound of formula (I) or its salt in it is 1 to 3,000 ppm.

* * * * *